United States Patent
Morris et al.

(10) Patent No.: US 9,592,088 B2
(45) Date of Patent: Mar. 14, 2017

(54) ELECTROSURGICAL INSTRUMENT AND SHAFT

(71) Applicant: GYRUS MEDICAL LIMITED, Cardiff (GB)

(72) Inventors: David Morris, Rhondda (GB); Louise Murphy, Cardiff (GB); Richard John Hoodless, South Gloucestershire (GB); Richard John Keogh, Caerphilly (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 415 days.

(21) Appl. No.: 14/106,034

(22) Filed: Dec. 13, 2013

(65) Prior Publication Data
US 2014/0171937 A1    Jun. 19, 2014

(30) Foreign Application Priority Data
Dec. 14, 2012    (GB) .................. 1222623.9

(51) Int. Cl.
*A61B 18/14*    (2006.01)
*A61B 18/12*    (2006.01)

(52) U.S. Cl.
CPC .......... *A61B 18/14* (2013.01); *A61B 18/1206* (2013.01); *A61B 18/1492* (2013.01); *A61B 2218/007* (2013.01)

(58) Field of Classification Search
CPC ... A61B 18/1492; A61B 18/14; A61B 18/082; A61B 18/1402; A61B 2018/00982;
(Continued)

(56) References Cited

U.S. PATENT DOCUMENTS 5,441,499 A * 8/1995 Fritzsch .......... A61B 17/00234
606/45
5,848,986 A * 12/1998 Lundquist .......... A61B 10/0233
604/164.11
(Continued)

FOREIGN PATENT DOCUMENTS

CN    101995653 A    3/2011
CN    102271598 A    12/2011
(Continued)

OTHER PUBLICATIONS

Search Report in GB1222623.9 dated Mar. 14, 2013.
(Continued)

*Primary Examiner* — Michael Peffley
(74) *Attorney, Agent, or Firm* — Nixon & Vanderhye PC

(57) ABSTRACT

A shaft (14) is provided for a flexible endoscopic instrument, the shaft including at least one flexible section (20) along the length of the shaft, a distal section (19) located distally of the flexible section, and a proximal section (18) located proximally of the flexible section (20). The distal section (19) includes a connection to a shaft electrode, while the proximal section (18) includes at least one connection for connecting the shaft (14) to an electrosurgical generator (1). The shaft also includes a bypass lead (26) in electrical connection with both the distal section (19) and the proximal section (18). The bypass lead (26) ensures that the distal section (19) and the proximal section (18) remain at the same potential even if the electrical pathway via the flexible section (20) becomes degraded by wear or damage thereto.

20 Claims, 4 Drawing Sheets

(58) Field of Classification Search
CPC A61B 2018/00172; A61B 2018/00494; A61B 2018/00488; A61B 2018/162; A61B 1/0055; A61B 1/015; A61B 1/00114; A61B 1/008; A61B 1/0124
See application file for complete search history.

(56) References Cited

U.S. PATENT DOCUMENTS

| | | | |
|---|---|---|---|
| 6,193,717 B1* | 2/2001 | Ouchi | A61B 18/1477 604/114 |
| 6,238,392 B1* | 5/2001 | Long | A61B 18/1485 604/101.05 |
| 6,283,960 B1 | 9/2001 | Ashley | |
| 6,602,248 B1* | 8/2003 | Sharps | A01N 43/52 604/114 |
| 6,726,684 B1* | 4/2004 | Woloszko | A61B 18/148 606/32 |
| 2009/0171159 A1 | 7/2009 | Jorgensen et al. | |
| 2010/0087818 A1 | 4/2010 | Cunningham | |
| 2010/0168721 A1 | 7/2010 | Rogers et al. | |
| 2011/0009863 A1 | 1/2011 | Marczyk et al. | |
| 2011/0034765 A1 | 2/2011 | Wehrheim | |

FOREIGN PATENT DOCUMENTS

| | | |
|---|---|---|
| EP | 0667126 | 8/1995 |
| EP | 2281499 | 2/2011 |
| WO | 96/39966 | 12/1996 |
| WO | 00/74555 | 12/2000 |
| WO | 2007/126888 | 11/2007 |
| WO | 2012/136957 A | 10/2012 |

OTHER PUBLICATIONS

European Search Report EP 13 19 4887 mailed Mar. 14, 2014.
Office Action dated Dec. 19, 2016 in Chinese Application No. 201310756723.X (8 pages).
English Translation of Office Action dated Dec. 19, 2016 in Chinese Application No. 201310756723.X (10 pages).

* cited by examiner

ELECTROSURGICAL INSTRUMENT AND SHAFT

This application claims priority to GB Application No. 1222623.9, filed 14 Dec. 2012, the entire contents of which is hereby incorporated herein by reference.

TECHNICAL FIELD

This invention relates to a flexible electrosurgical instrument and to a flexible shaft for such an electrosurgical instrument. Such systems are commonly used for the vaporisation and/or coagulation of tissue in surgical intervention, most commonly in "keyhole" or minimally invasive surgery, otherwise known as "endoscopic" surgery.

BACKGROUND TO THE INVENTION AND PRIOR ART

One specialist type of electrosurgical instrument has one or more electrosurgical electrodes at the distal end of a flexible shaft. Such an instrument is particularly suited to the treatment of joints, particularly the hip joint, as the articulation of the shaft allows the electrodes to reach otherwise inaccessible areas of the joint. U.S. Pat. No. 6,283,960 is one example of this type of instrument.

The shaft typically contains at least one section with greater flexibility than other sections of the shaft. This section of the shaft is normally manufactured to have lower bending stiffness, or with a "weak section", with less material being present so as to provide greater flexibility. Typically material is removed to form slots, grooves or other cut-outs, to enable the shaft to flex more easily at this section of the shaft.

SUMMARY OF THE INVENTION

Embodiments of the present invention provide an improvement to the above described type of instrument.

Accordingly, from one aspect of the invention there is provided a shaft for a flexible endoscopic instrument, the shaft having a longitudinal axis defining a proximal and a distal direction, and including a) at least one flexible section along the length of the shaft, the flexible section having a greater flexibility than at least one other section of the shaft, b) a distal section located distally of the flexible section, the distal section including a connection to a shaft electrode, c) a proximal section located proximally of the flexible section, the proximal section including at least one connection for connecting the shaft to an electrosurgical generator, and d) a bypass lead including a first connection forming an electrical connection with the distal section and a second connection forming an electrical connection with the proximal section.

Typically, the at least one flexible section includes one or more cut-out portions, such as a plurality of slots cut into the shaft. The shaft is typically a tubular shaft.

It should be remembered that the shaft provides an electrical connection between the shaft electrode and the electrosurgical generator. However, the flexible section is also subjected to repeated flexing, and such repeated flexing can cause cracks to form which interfere with the passage of electric current along the shaft. There is a risk that these cracks can form to such an extent that areas of the shaft become electrically isolated one from another, such that they are at a different electric potential one from another. In extreme cases, where different areas of the shaft are at different potentials, arcing can occur between different sections of the shaft, causing damage to the shaft and potentially to the patient. The provision of the bypass lead ensures that each end of the shaft remains electrically connected to the other end and at the same potential, regardless of whether cracks have formed therebetween. The bypass lead prevents arcing from occurring between different sections of the shaft, even if cracks have formed in some sections thereof.

In one convenient arrangement, the bypass lead is directly connected to the distal section of the shaft, typically by being welded to the distal section of the shaft. Similarly, the bypass lead is conveniently directly connected to the proximal section of the shaft, again typically by welding. However, in an alternative arrangement, the bypass lead is indirectly connected to the proximal section of the shaft. In this arrangement the bypass lead is not connected directly to the proximal section of the shaft, but to some other component which is itself in electrical connection to the proximal section of the shaft. Conveniently, the at least one connection for connecting the shaft to an electrosurgical generator comprises a generator cord, and the bypass lead is connected to the generator cord. Regardless of whether they are directly connected, the bypass lead electrically connects the proximal and distal sections one to the other, such that they are always at the same electric potential. In this way, there is no possibility of unwanted arcing occurring between sections of the shaft, even if cracks or other imperfections are introduced due to the repeated flexing of the shaft.

The shaft electrode is conveniently constituted by an exposed surface of the shaft. In this way, the shaft itself forms the electrode, which can either be the tissue treatment electrode in a monopolar system, or one of a pair of electrodes (typically the return electrode) in a bipolar system. Alternatively, the shaft can provide the electrical connection for a separate tissue treatment or return electrode, which is electrically connected to the shaft by means of a connection such as a lead or clip arrangement. Whichever arrangement is employed, the shaft provides the electrical pathway for the current to reach the electrode (or return to the generator therefrom), and the bypass lead ensures a good connection is maintained.

From another aspect there is further provided an electrosurgical instrument comprising a) a shaft having a longitudinal axis defining a proximal and a distal direction, the shaft including at least one flexible section along the length of the shaft, the flexible section having a greater flexibility than at least one other section of the shaft, the shaft also including a distal section located distally of the flexible section, and a proximal section located proximally of the flexible section, b) a shaft electrode electrically connected to the distal section of the shaft, c) an electrical connection for connecting the proximal section of the shaft to an electrosurgical generator, and d) an actuation mechanism for causing the shaft to articulate at the at least one flexible section, characterised in that the shaft also includes a bypass lead including a first connection forming an electrical connection with the distal section and a second connection forming an electrical connection with the proximal section.

As previously indicated, the shaft electrode is conceivably constituted by an exposed surface of the shaft. Alternatively the instrument also includes a tissue-treatment electrode, the shaft electrode constituting a return electrode for the tissue-treatment electrode.

BRIEF DESCRIPTION OF THE DRAWINGS

Embodiments of the invention will now be further described, by way of example only, with reference to the accompanying drawings, in which.

DESCRIPTION OF THE EMBODIMENTS

Figure 1:
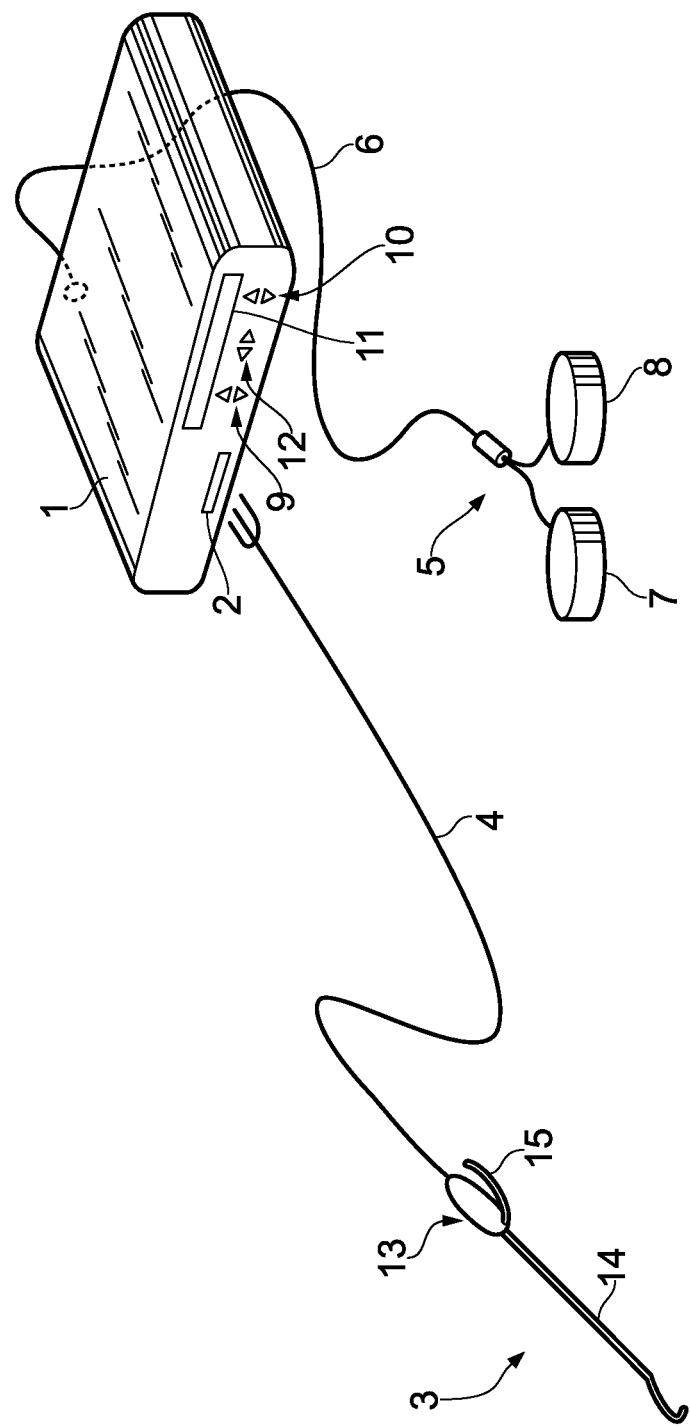
FIG. 1 is a schematic diagram of an electrosurgical system in accordance with an embodiment of the present invention.

Referring to the drawings, FIG. 1 shows an electrosurgical apparatus including a generator 1 having an output socket 2 providing a radio frequency (RF) output, via a connection cord 4, for an electrosurgical instrument 3. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a desiccation mode and a vaporisation mode of the generator 1 respectively. The generator front panel has push buttons 9 and 10 for respectively setting desiccation and vaporisation power levels, which are indicated in a display 11. Push buttons 12 are provided as an alternative means for selection between the desiccation and vaporisation modes.

The electrosurgical instrument 3 comprises a housing 13 with an elongate shaft 14, and one or more tissue treatment electrodes at the distal end of the shaft, as will be described below. A movable handle 15 associated with the housing can be actuated to cause the shaft to bend. This instrument is particularly suited to the treatment of the hip joint, where a relatively long shaft with articulation capability is needed to access the area to be treated.

Figure 2:
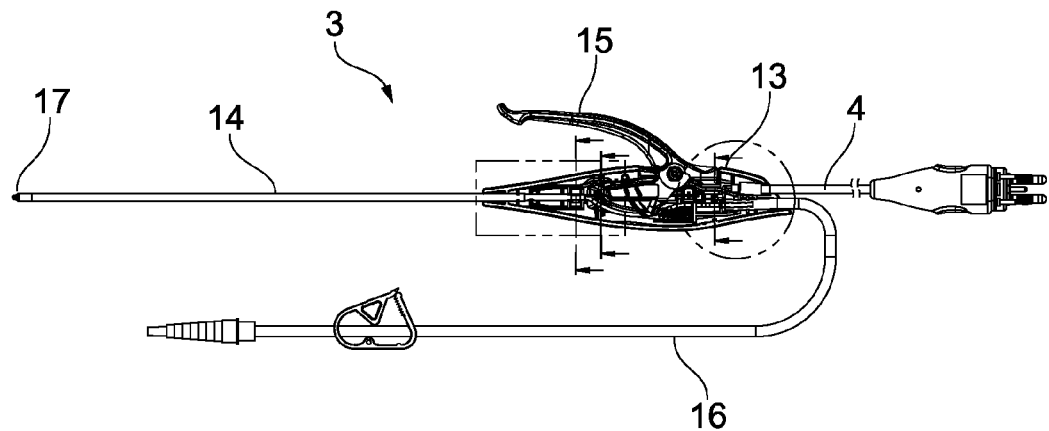
FIG. 2 is a side view of the tip of the electrosurgical instrument forming part of the system of FIG. 1.

FIG. 2 shows the instrument 3 in more detail, and the housing 13, the handle 15 and the elongate shaft 14. The connection cord 4 is shown emerging from the proximal end of the housing, as is a suction tube 16 which can be connected to a source of suction (not shown) in order to deliver suction to the shaft 14 and hence the tip 17 of the instrument.

Figure 3:
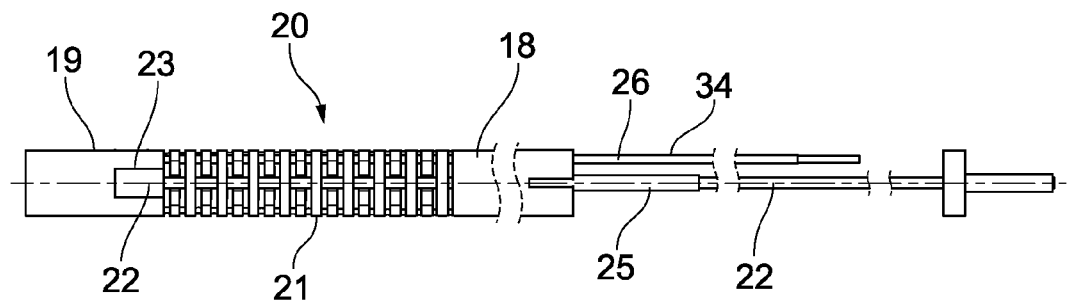
FIG. 3 is a cut-away plan view of the shaft of the instrument of FIG. 2.
Figure 4:
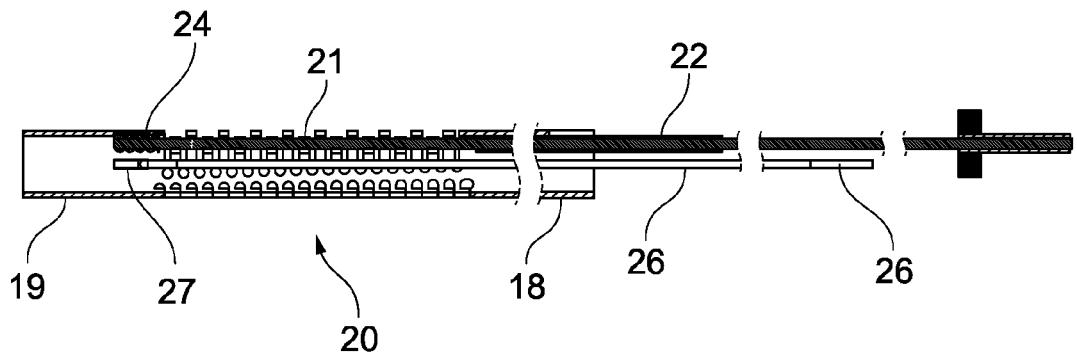
FIG. 4 is a cut-away side view of the shaft of FIG. 3.

FIGS. 3 & 4 show the shaft 14 of the instrument 3 as comprising a proximal section 18, a distal section 19, and a flexible section 20 therebetween. The flexible section 20 is constituted by a plurality of slots 21 extending partially around the circumference of the shaft in order to impart flexibility thereto. A nitinol (a nickel-titanium alloy where the two metals are present in substantially equal atomic percentages) deflection wire 22 extends along the shaft 14 and is encased in a crimped casing 23 towards its distal end, as further shown in FIG. 5. The casing 23 is welded to the distal section 19 as shown at 24, and the shaft 14 is surrounded with a metallic shroud 33. The exterior of the shaft 14 is covered with an insulating sheath 35. The deflection wire 22 is also encased in a guide tube 25 at its proximal end, and continues into the housing such that a longitudinal movement of the deflection wire 22 causes a corresponding deflection of the shaft 14.

Figure 5:
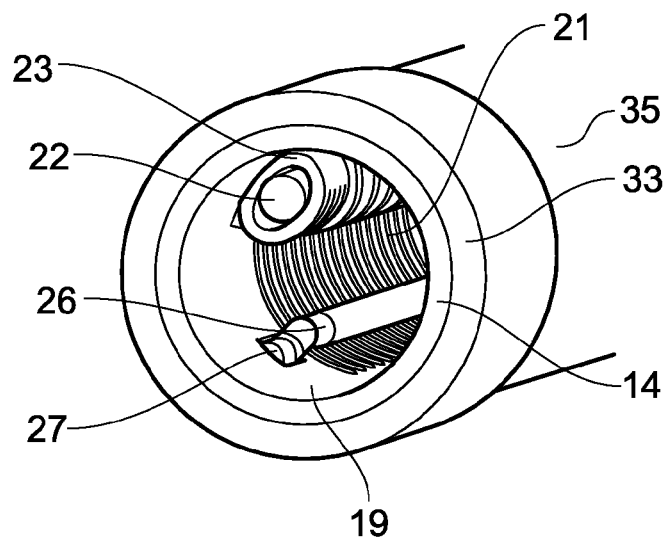
FIG. 5 is a perspective end view of the shaft of FIG. 3.

Also shown in FIGS. 3, 4 & 5 is an electrical bypass wire 26, which runs along the shaft 14 connecting the distal section 19 to the proximal section 18. The bypass wire is covered with an insulating sheath 34, except for its ends, which are exposed. The distal end of the bypass wire 26 is welded to the distal section 19 as shown at 27. The proximal end of the bypass wire extends past the flexible section 20 and the proximal section 18 to emerge from the proximal end of the shaft.

Figure 6:
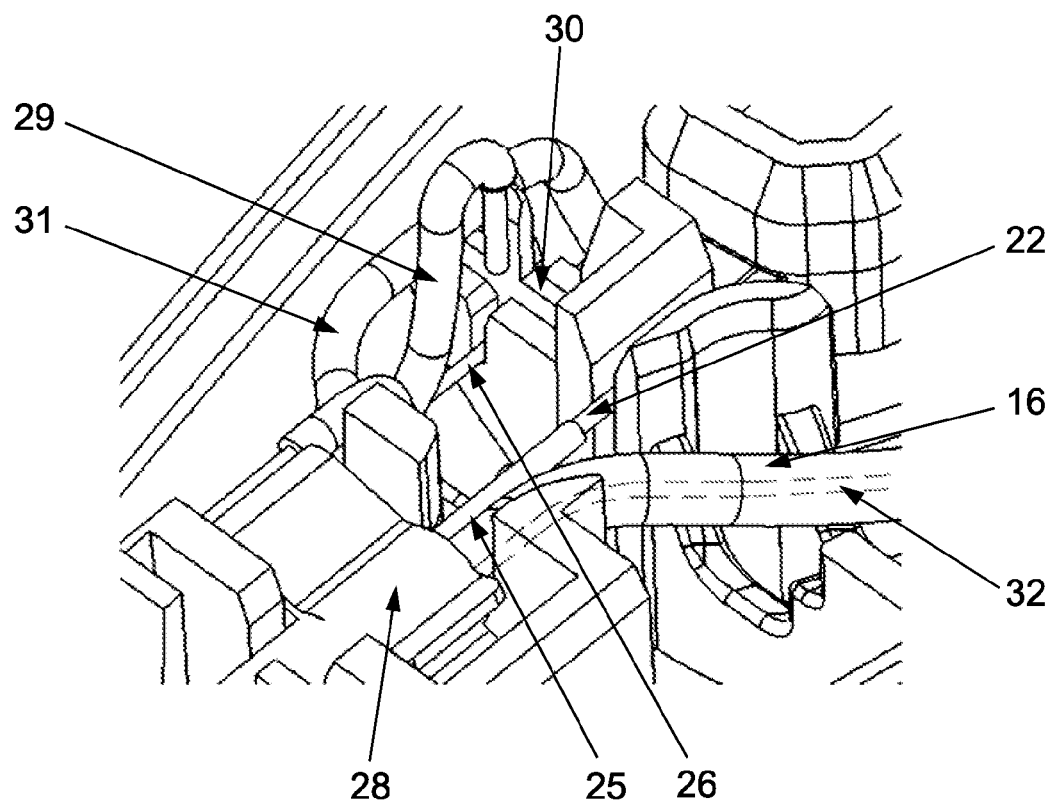
FIG. 6 is a cut-away perspective view, with hidden detail, of a part of the instrument of FIG. 2.
Figure 7:
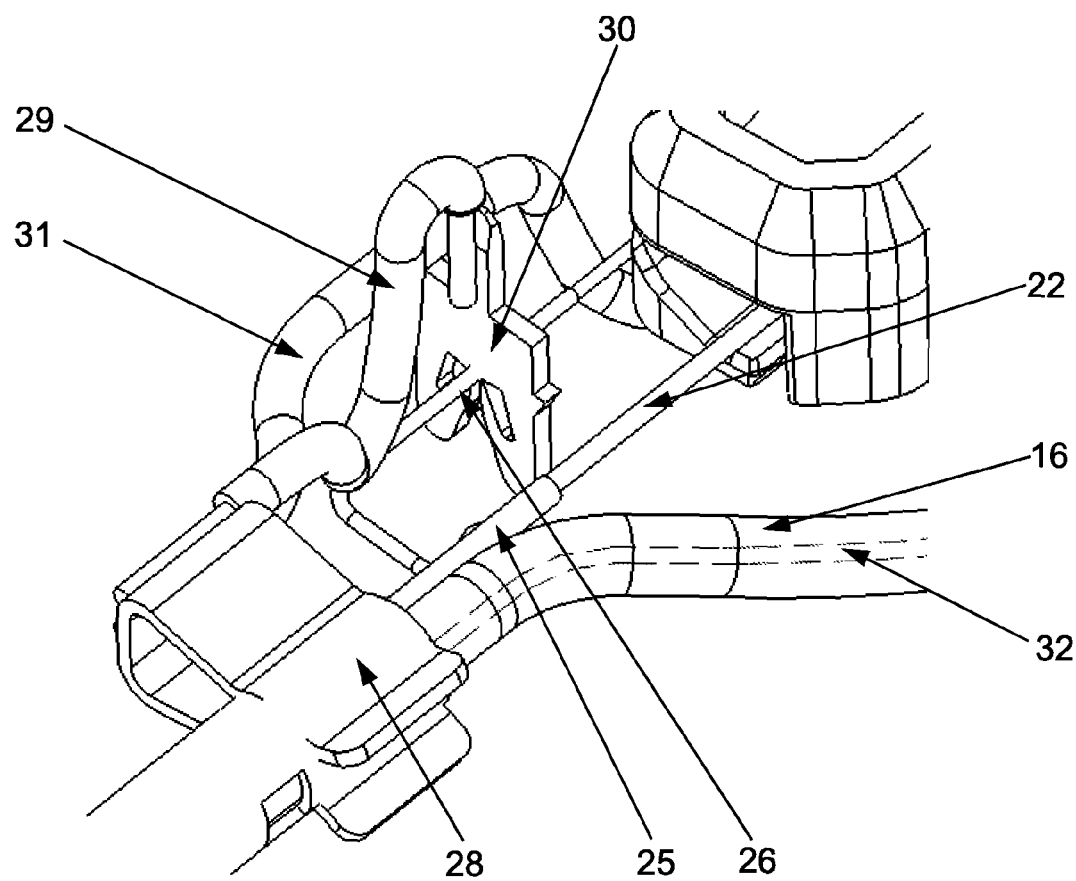
FIG. 7 is a cut-away perspective view similar to FIG. 6, but with the handle moulding of the instrument removed for clarity.

The proximal connection of the bypass wire 26 is shown in FIGS. 6 & 7. A metallic clip 28 is fitted over the proximal section 18 of the shaft 14, and a wire 29 connects the clip 28 to a Siamese connector 30. The Siamese connector 30 connects the wire 29, and hence the shaft 14, to the bypass wire 26. In this way, the proximal section of the bypass wire 26 is electrically connected to the proximal section 18 of the shaft, while the distal section of the bypass wire is welded to the distal section 19 of the shaft as previously described. Thus, the bypass wire is in electrical connection with each end of the shaft, and ensures that they remain at the same electric potential, regardless of the electrical connection along the shaft itself.

A lead 31 connects the shaft 14 to the cord 4 leading to the generator 1, such that the shaft itself (or a separate electrode (not shown) attached to the shaft) acts as an electrode in either a monopolar or bipolar electrode assembly. In a monopolar arrangement, the shaft (or the separate electrode) acts as the tissue-treatment electrode, while a patient return plate (not shown) acts as the return electrode. In a bipolar arrangement, as shown in FIG. 6, a lead 32 running through the suction tube 16 forms a connection between the generator 1 and an active tissue treatment electrode (not shown), while the shaft (or the separate electrode) acts as the return electrode. Whichever arrangement is employed, the electrode assembly can be used to treat tissue while the bypass wire 26 ensures that each end of the shaft remains at the same electric potential even if the direct path between the proximal and distal sections of the shaft becomes interrupted by cracks or other damage caused by the repeated flexing of the flexible section 20.

In use, the instrument 3 is manoeuvred into position adjacent tissue to be treated, using the deflection wire 22 to deflect the flexible section 20 of the shaft into a curved shape if required. The electrosurgical generator 1 is activated in order to supply RF energy to the electrode assembly at the tip 17 of the instrument, with the shaft 14 either forming an electrode at the tip of the instrument or acting as the electrical connection to such an electrode. The bypass wire 26 ensures that, even if electrical conductivity between the proximal section 18 and the distal section 19 of the shaft becomes degraded by wear or damage to the flexible section 20, all areas of the shaft remain at the same electric potential such that arcing does not occur across gaps that may have formed following cracking of material around the slots 21.

The instrument 3 is primarily designed to be operated in a conductive fluid such as saline, with the fluid completing the circuit between the electrodes. However, the instrument 3 can also be used as a dry-field instrument, in which case the user must ensure that the electrodes are placed in contact with the tissue to be treated. In this way, the current flows from the tissue treatment electrode, through the tissue, to the shaft 14 which acts as a return electrode.

Various modifications, whether by way of addition, deletion, or substitution may be made to the above described embodiment to provide further embodiments, any and all of which are intended to be encompassed by the appended claims.

The invention claimed is:

1. A shaft for a flexible endoscopic instrument, the shaft having a longitudinal axis defining a proximal direction and a distal direction, and including:
   at least three discrete sections along the length of the shaft, namely a proximal section, a distal section and a flexible section between the proximal section and the distal section,
   the shaft being an electrode and acting as a tissue treatment electrode, or as a return electrode where the instrument is provided with a tissue treatment electrode which is separate from the shaft,
   the flexible section having a greater flexibility than either the proximal section or the distal section,
   the distal section being located distally of the flexible section, the distal section being a part of the shaft electrode when acting as a tissue treatment electrode that is used to engage tissue being treated,
   the proximal section being located proximally of the flexible section, the proximal section including at least one connection for electrically connecting the shaft to an electrosurgical generator, and
   a bypass lead including a first connection forming an electrical connection with the distal section and a second connection forming an electrical connection with the proximal section whereby the bypass lead electrically interconnects the proximal section only to the distal section to thereby provide, as a second connection, that the proximal and distal sections remain at a same electric potential, regardless of whether an electrical connection along the flexible section becomes degraded by wear or damage to the flexible section.

2. The shaft according to claim 1, wherein the flexible section includes one or more cut-out portions to make the flexible section flexible.

3. The shaft according to claim 2, wherein the one or more cut-out portions comprise a plurality of slots cut into the shaft.

4. The shaft according to claim 1, wherein the shaft is tubular.

5. The shaft according to claim 1, wherein the bypass lead is directly connected to the distal section of the shaft.

6. The shaft according to claim 5, wherein the bypass lead is welded to the distal section of the shaft.

7. The shaft according to claim 1, wherein the bypass lead is directly connected to the proximal portion of the shaft.

8. The shaft according to claim 7, wherein the bypass lead is welded to the proximal portion of the shaft.

9. The shaft according to claim 1, wherein the bypass lead is indirectly connected to the proximal section of the shaft.

10. The shaft according to claim 9, wherein the at least one connection for connecting the shaft to an electrosurgical generator comprises a generator cord, and the bypass lead is connected to the generator cord.

11. The shaft according to claim 1, wherein the shaft tissue treatment electrode is constituted by an exposed surface of the shaft.

12. The shaft according to claim 1, wherein the shaft is provided with the separate tissue-treatment electrode, such that the shaft electrode constitutes the return electrode for the separate tissue-treatment electrode.

13. The shaft according to claim 1, wherein the shaft is constructed to be used as the tissue-treatment electrode in a monopolar electrode assembly where a patient return plate acts as the return electrode.

14. An electrosurgical instrument comprising
   a shaft having a longitudinal axis defining a proximal and a distal direction, the shaft including at least one flexible section along the length of the shaft, a distal section located distally of the flexible section, and a proximal section located proximally of the flexible section, the at least one flexible section having a greater flexibility than either the proximal section or the distal section of the shaft,
   a shaft electrode electrically connected to the distal section of the shaft,
   an electrical connection for connecting the proximal section of the shaft to an electrosurgical generator, wherein the shaft acts as an electrical connection to the shaft electrode from the electrosurgical generator,
   an actuation mechanism for causing the shaft to articulate at the at least one flexible section when the actuation mechanism is activated, and
   a bypass lead including a first connection forming an electrical connection with the distal section and a second connection forming an electrical connection with the proximal section, whereby the bypass lead electrically interconnects the proximal section only to the distal section to thereby provide, as a second connection, that the proximal and distal sections remain at a same electric potential, regardless of whether an electrical connection along the flexible section becomes degraded by wear or damage to the flexible section.

15. The electrosurgical instrument according to claim 14, wherein the shaft electrode is constituted by an exposed surface of the shaft.

16. The electrosurgical instrument according to claim 14, wherein the instrument also includes a tissue-treatment electrode which is separate from the shaft electrode and separately electrically connected to the electrosurgical generator, whereby the shaft electrode connected to the shaft acts as a return electrode for the separate tissue-treatment electrode.

17. The electrosurgical instrument according to claim 14, wherein the shaft electrode is constructed to be used as a tissue-treatment electrode in a monopolar electrode assembly where a patient return plate acts as a return electrode.

18. An electrosurgical instrument comprising:
   a housing,
   a suction tube emerging from a proximal end of the housing, and
   an elongate shaft extending from a distal end of the housing,
   the shaft being electrically connected to an electrosurgical generator, and acting as either a tissue treatment electrode, or as a return electrode where a tissue treatment electrode separate from the shaft is provided at a distal end of the shaft and the separate tissue treatment electrode is connected by a separate electrical lead extending from the generator,
   the elongate shaft comprising:
     a proximal section,
     a distal section, and
     a flexible section between the proximal section and the distal section, the flexible section having a flexibility greater than a flexibility of the proximal section and a flexibility of the distal section of the shaft, the flexible section being constituted by a plurality of slots extending partially around a circumference of the shaft to thereby impart flexibility to the flexible section, the distal section being constructed for interaction with the tissue being treated by the instrument, where the shaft acts as the tissue treatment electrode, the proximal section being electrically connected to the electrosurgical generator, and a bypass lead including a first connection forming an electrical connection with the distal section electrical connection and a second connection forming an electrical connection with the proximal section electrical connection, whereby the bypass lead electrically interconnects the proximal section only to the distal section to thereby provide, as a second connection, that the proximal and distal sections remain at a same electric potential, regardless of whether an electrical connection along the flexible section becomes degraded by wear or damage to the flexible section.

19. The electrosurgical instrument according to claim 18, wherein the housing has a movable handle associated with it that can be actuated so as activate an actuation mechanism to thereby cause the flexible section and thereby the elongate shaft to bend.

20. The electrosurgical instrument according to claim 18, wherein the separate electrical lead connecting the separate tissue treatment electrode to the generator runs through the suction tube.

* * * * *